United States Patent
De Groof et al.

(10) Patent No.: US 11,291,715 B2
(45) Date of Patent: Apr. 5, 2022

(54) DILUENT FOR CELL-ASSOCIATED ALPHAHERPESVIRUS VACCINE

(71) Applicant: Intervet Inc., Madison, NJ (US)

(72) Inventors: Ad De Groof, Boxmeer (NL); Iwan Verstegen, Boxmeer (NL)

(73) Assignee: Intervet Inc., Madison, NJ (US)

(*) Notice: Subject to any disclaimer, the term of this patent is extended or adjusted under 35 U.S.C. 154(b) by 0 days.

(21) Appl. No.: 16/771,022

(22) PCT Filed: Dec. 19, 2018

(86) PCT No.: PCT/EP2018/085801
§ 371 (c)(1),
(2) Date: Jun. 9, 2020

(87) PCT Pub. No.: WO2019/121888
PCT Pub. Date: Jun. 27, 2019

(65) Prior Publication Data
US 2021/0162036 A1  Jun. 3, 2021

(30) Foreign Application Priority Data
Dec. 20, 2017 (EP) .................................... 17208992

(51) Int. Cl.
*A61K 39/12* (2006.01)
*A61K 39/00* (2006.01)

(52) U.S. Cl.
CPC ...... *A61K 39/12* (2013.01); *A61K 2039/5156* (2013.01); *A61K 2039/5254* (2013.01); *A61K 2039/70* (2013.01)

(58) Field of Classification Search
None
See application file for complete search history.

(56) References Cited

U.S. PATENT DOCUMENTS

| | | | | |
|---|---|---|---|---|
| 4,160,024 A * | 7/1979 | Schat | ............ | A61K 39/255 424/229.1 |
| 4,980,162 A * | 12/1990 | Honda | ............ | A61K 39/245 424/202.1 |
| 5,378,467 A | 1/1995 | Bexendale | | |
| 10,786,565 B2 * | 9/2020 | Teague | ............ | A61K 39/255 424/229.1 |
| 2010/0098725 A1 * | 4/2010 | Liu | ............ | A61P 31/16 424/209.1 |

FOREIGN PATENT DOCUMENTS

| RU | 2179035 C1 | 2/2002 |
|---|---|---|
| WO | 9314195 A1 | 7/1993 |

OTHER PUBLICATIONS

Howell et al. (Journal of Clinical Microbiology. 1983; 18 (3): 658-662).*
March (Vaccine; 2004; 22: 4358-4364).*
Bovarnick, M.R., et al., The Influence of certain salts, amino acids, sugars, and proteins on the stability of Rickettsiae, J. Bacteriol., Jan. 13, 1950, pp. 509-522, vol. 59.
Calnek, B.W. et al., Lyophilization of Cell-Free Marek's Disease Herpesvirus and a Herpesvirus from Turkeys, Applied Microbiology, 1970, 723-726, 20(5).
Colwell, W.M. et al., Influence of Some Physical Factors on Survival of Marek's Disease Vaccine Virus, Avian Diseases, 1975, 781-790, 19(4).
Damm, Philip G., Processing Marek's Disease Vaccine, Bulletin of the Parenteral Drug Association, 1974, 98-102, 28.
European Search report for 17208992.2, dated Jun. 4, 2018, 12 pages.
Geerligs, H.J., and Hoogendam, A., Determination of Optimal Conditions for Thawing and Diluting Cell-Bound CVI 988 Marek's Disease Vaccine and Stability of the Diluted Vaccine, Avian Diseases, 2007, pp. 969-973, vol. 51, No. 4.
International Search Report and Written Opinion for PCT/EP2018/085801 dated Feb. 27, 2019, 18 pages.
Nicholas, R.A.J., et al., A comparison of titration methods for Marek's disease vaccines, Journal of Biological Standardization, 1979, pp. 43-51, vol. 7, No. 1.
Reddy, S.M., et al., Marek's disease vaccines: Current status, and strategies for improvement and development of vector vaccines, Veterinary Microbiology, 2017, pp. 113-120, vol. 206.
Schat, Karel A., History of the First-Generation Marek's Disease Vaccines: The Science and Little- Known Facts, Avian Diseases, 2016, 715-724, 60(4).
Sigma Aldrich Product information sheet for N-Z-Amine A, XP-002780959.
Zanella, A. et al., Marek's disease control: Comparative efficacy of cell-associated and cell-free lyophilized HVT vaccine, Avian Pathology, 1974, 45-50, 3(1).

* cited by examiner

*Primary Examiner* — Shanon A. Foley
(74) *Attorney, Agent, or Firm* — Michael D. Davis

(57) ABSTRACT

The present invention relates to the use of a diluent for the in-use stabilisation of cells infected with a cell-associated alphaherpesvirus. Contrary to the long-standing practice of incorporating a considerable amount of peptone into the diluent for such virus-infected cells, it was found that a reduction of the amount of protein in the diluent improved the in-use stability of alphaherpesvirus-infected cells. Whereby the best stability was even obtained using a protein-free diluent. This effect was especially pronounced for recombinant HVT viruses expressing a heterologous insert. Being protein-free is highly advantageous for the production of the diluent, in respect of costs, safety, and consistency of production.

15 Claims, No Drawings

DILUENT FOR CELL-ASSOCIATED ALPHAHERPESVIRUS VACCINE

CROSS-REFERENCE TO RELATED APPLICATIONS

This application is a national stage entry under 35 U.S.C. § 371 of PCT/EP2018/085801, filed on Dec. 19, 2018, which claims priority to EP17208992.2 filed on Dec. 20, 2017, the content of PCT/EP2018/085801 is hereby incorporated by reference in its entirety.

The present invention relates to the field of vaccinology, more specifically the invention relates to the use of a diluent for the in-use stabilisation of cells infected with a cell-associated alphaherpesvirus, further the invention relates to a process for said in-use stabilisation, to a vaccine against cell-associated alphaherpesvirus, and to a process for the preparation of said vaccine.

Alphaherpesviruses are important pathogens for humans and almost all animal species on earth, and thus also for animal species of relevance to commercial farming. The method of choice for providing cheap and effective protection from infection and disease is by vaccination. For example in commercial poultry farming operations it is common practice to vaccinate the birds against Marek's disease and infectious laryngotracheitis, both highly relevant diseases in the poultry industry regarding animal welfare and economy of operation. Details are described e.g. in handbooks, like: The Merck veterinary manual (2010, 10th ed., 2010, C. M. Kahn edt., ISBN: 091191093X), and: 'Disease of poultry' (2008, 12$^{th}$ ed., Y. Saif ed., Iowa State Univ. press, ISBN-10: 0813807182).

Avian laryngotracheitis is a respiratory disease of poultry caused by infectious laryngotracheitis virus (ILTV), also known as gallid herpesvirus 1, or avian herpesvirus 1. ILTV belongs to the genus Iltovirus of the alphaherpesvirinae subfamily. Infection causes respiratory distress accompanied by gasping and expectoration of bloody exudate. An infection with ILTV spreads rapidly and can affect up to 100% of an infected flock. The disease may cause reduction in egg production, weight loss, increased sensitivity to secondary infection, and even generalised mortality. Live attenuated vaccines exist for ILTV, but these carry the potential danger of residual virulence, or reversion to virulence. Recently vector based vaccines have been described such as Innovax™-ILT, see below.

Marek's disease is a highly infectious disease of poultry, and occurs worldwide. Typical signs of disease are T-cell lymphomas in several organs and nerves. This may lead to a variety of symptoms, among others paralysis and mortality, but also egg production losses and condemnations at slaughter. Marek's disease is caused by Marek's disease virus (MDV) which belongs to the genus Mardivirus in the alphaherpesvirinae subfamily.

MDVs have been taxonomically classified based on biologic- and serologic properties into three main serotypes: MDV serotype 1 (MDV1), also known as gallid herpesvirus 2, is the main cause of Marek's disease as it is oncogenic for poultry, and different pathotypes have been described from mild to very virulent. Attenuated MDV1 strains have been developed that are used in attenuated live viral vaccines, examples of MDV1 strains are RB1B, 814, and CVI-988 Rispens (Cui et al., 2013, PLoS One, vol. 8: e53340), for example as in: Nobilis™ Rismavac (MSD Animal Health).

MDV serotype 2 (MDV2), also known as gallid herpesvirus 3, is only of little pathogenicity to poultry. Live vaccine strains have been developed, e.g. based on strain SB1 (Petherbridge et al., 2009, J. Virol. Meth., vol. 158, p. 11), for example as in Nobilis™ Marexine SB1 (MSD Animal Health).

Finally, MDV serotype 3 is also known as meleagrid herpesvirus 1, but is commonly called: herpesvirus of turkeys (HVT). HVT was first described in 1970 (Witter et al., 1970, Am. J. Vet. Res., vol. 31, p. 525), and is a pathogenic. Interestingly however, vaccination with HVT provides a cross-protective immunity against serotype 1 and 2 MDV, making this virus naturally suitable as the basis of a live vaccine against MDV1 and 2. As a result, vaccination with HVT is currently applied to almost every new-born chick in agriculture, resulting in up to 5 Billion doses of HVT vaccine being administered annually across the world.

HVT vaccines are commonly based on strains such as PB1 or FC-126, for example as in Nobilis™ Marexine CA126 (MSD Animal Health).

When protection against very virulent variants of MDV is required, combination vaccines may be applied of HVT vaccine with an MDV1- or MDV2 vaccine-strain.

MDV vaccines are for example described in European Pharmacopoeia monograph 0589, of April 2013.

HVT and MDV replicate in a birds' peripheral blood lymphocytes and induce an immune response of long duration. This is also applied in the use of MDV or HVT as a viral vector-vaccine for the expression and delivery to poultry of various immunogenic proteins from other avian pathogens, see e.g. WO 87/04463 and WO 2013/082317. Through the years many heterologous genes have been expressed in these vectors, such as the fusion protein gene (F-gene) from Newcastle disease virus (NDV) (Sondermeijer et al., 1993, Vaccine, vol. 11, p. 349-358); the viral protein 2 (VP2) gene of infectious bursal disease virus (IBDV) (Darteil et al., 1995, Virology, vol. 211, p. 481-490); the glycoprotein D and I protein genes (gD/gI) of ILTV; and the Ea1a gene for an Eimeria parasite surface antigen (Cronenberg et al., 1999, Acta Virol., vol. 43, p. 192-197).

This has led to a variety of commercial HVT vector-vaccine products, for instance: with the NDV-F gene: Innovax™ ND, and Vectormune™ HVT-NDV (Ceva); the IBDV VP2 gene: Vaxxitek™ HVT+IBD (Merial; previously named: Gallivac™ HVT-IBD), and Vectormune™ HVT-IBD (Ceva); and with the ILTV gD/gI genes in Innovax™ LT. All Innovax vaccines are from MSD Animal Health.

Even multiple inserts of heterologous genes into HVT are possible, for example of the NDV-F and the IBDV-VP2 genes as in Innovax™ ND-IBD. Also HVT vector vaccines can in turn be combined with classic MDV vaccine strains of MDV serotype 1 or 2, such as in Innovax™ ND-SB.

Alternatively an HVT vector can be used for the expression and delivery of a therapeutic protein, e.g. a cytokine, to manipulate the chicken's immune response (WO 2009/156.367; and Tarpey et al., 2007, Vaccine, vol. 25, p. 8529-8535).

Several alphaherpesviruses are to some extent cell-associated viruses; examples are varicella zoster virus, ILTV, MDV, and HVT. Such viruses do not (fully) lyse their host cell upon completion of their replication. Consequently, this type of virus spreads within an infected host animal via cell to cell contact. Spread to other animals occurs by transfer of infected cells; for example for MDV and HVT this means that virus infection in vivo spreads via inhalation of infected skin cells that are shed from the feather follicles of infected birds.

New-born chicks face infective pressure of MDV from their first day of age. Fortunately HVT and HVT-vector vaccines can be applied to chickens at a very early age, as they are safe and (when cell-associated) relatively insensitive to maternally derived antibodies. Consequently, HVT vaccines are inoculated into chicks at the day of their hatching from the egg (day one), or even before hatching, while still in the egg. This last approach, so-called 'in ovo vaccination', is a form of embryo vaccination, which (for chickens) is commonly applied at day 18 of embryonic development (ED), about 3 days before hatch. This type of vaccination is now commonly performed using automated equipment.

The first HVT vaccines were developed at the end of the 1960's. A historical overview is provided by Schat (2016, Avian Dis., vol. 60, p. 715-724). Initially the main focus was on developing cell-free, lyophilised vaccines. In this type of vaccine, the cell-free HVT was prepared and stabilised in a buffer called SPGA for: sucrose, phosphate, glutamate, and albumin (Calnek et al., 1970, Appl. Microbiol., vol. 20, p. 723-726). SPGA contains: sucrose: 218 mM (74.6 mg/ml); monopotassium phosphate: 3.8 mM (0.52 mg/ml); dipotassium phosphate: 7.2 mM (1.26 mg/ml); monosodium glutamate: 4.9 mM; and 1% w/v bovine albumin, in high-grade water. Optional variants of SPGA were the addition of 0.2% w/v sodium ethylene diamine-tetraacetic acid (EDTA), and/or the replacement of the 1% BSA by a protein hydrolysate at the same concentration. Alternatively BSA could be replaced by gelatine, or polyvinyl-pyrrolidone. Even plain sucrose-phosphate buffers have been described for reconstituting lyophilised HVT vaccines.

However it was quickly realised that the efficacy of lyophilised MDV vaccines was not as good as that for cell-associated vaccines. However such vaccine required much more complex precautions to stabilise not only the virus but also the infected host cell, such as the storage of the suspension of infected host cells in liquid nitrogen, and reconstitution in rich media to allow recovery of the cell's health after thawing. This is for example described in: Zanella & Granelli (1974, Avian Pathol., vol. 3, p. 45-50), and: Damm (1974, Bull. Parent. Drug Assoc., vol. 28, p. 98-102). Also, Colwell et al. (1975, Avian Dis., vol. 19, p. 781-790) compared a number of commercial diluents for cell-associated MDV vaccines, but no details are provided on their composition. The comparison was relative to TPB (tryptose phosphate broth), which has dextrose, salt, phosphate, and 2% w/v tryptose, which is a peptone (a mixture of amino acids and peptides) of bovine milk casein derived by enzymatic hydrolysis by pancreatic enzymes.

Geerligs & Hoogendam (2007, Avian Disease, vol. 51, p. 969-973) describe a study into the conditions for thawing and diluting cell-associated MDV1 vaccine of strain CVI-988. The diluents used are SPGA/EDTA or the commercial diluent of the Poulvac™ Marek vaccine (Zoetis). The 'summary of product characteristics' (SmPC) of Poulvac Marek describes the composition of this diluent as follows: Sucrose: 51.2 mg/ml (150 mM); (mono)potassium dihydrogen phosphate: 0.52 mg/ml (3.8 mM); (di)potassium monohydrogen phosphate: 1.26 mg/ml (7.2 mM); N-Z-Amine: 15 mg/ml (1.5% w/v); and pH indicator.

Similarly, the SmPC of the diluent for Nobilis™ vaccines: Nobilis™ Diluent CA describes its constituents as: "Sucrose, Pancreatic digest of casein, Monobasic potassium phosphate", and includes a pH indicator. In this diluent the concentration of the peptone is 1.4% w/v.

Since the mid 1970's vaccination with cell-associated MDV and HVT vaccines has become the standard in the poultry industry. This even though the production of cell-associated viruses of MDV, HVT, and HVT-based vectors, and shipping many millions of doses of these vaccines is very difficult because all processes have to be optimal both for the host cells and for the vaccine virus. Main issues are: the limited availability of suitable host cells, and the relative instability of the virus.

Regarding the host cells: proliferation of ILTV, MDV and HVT viruses is limited to avian cells. Of that type there are only few stable cell-lines available for in vitro culturing, and only very few on which these viruses grow to high titres. Therefore the culturing is commonly done on freshly prepared primary cells; for example fresh chicken embryo fibroblasts (CEF's) are prepared every few days, from 10 day old chicken embryo's using trypsin digestion. Next to being a laborious process, the quality of the primary cells may also display batch-to-batch variability. A promising development in this regard is the generation of a recombinantly immortalised line of CEF as described in WO 2016/087560.

Regarding stability: the cell-associated nature of these viruses is the critical factor, whereby virus survival depends to a large extent on the vitality of the host cells. While ILTV can quite readily be obtained as cell-free virus, for HVT and MDV this applies to (much) lesser extent, and these are (much) more stable when inside their host cell. So although cell-free lyophilised vaccines of MDV and HVT are available, the bulk of the commercial MDV and HVT vaccines, as well as the HVT-based vector-vaccines, is provided as a concentrated suspension of virus-infected cells that is packed in sealed glass-ampules, which are kept frozen and are stored in liquid nitrogen. Subsequently the 'cold chain' is maintained by shipping out the vaccines in containers of liquid nitrogen to end-users all over the world. Clearly this is logistically very demanding.

Inappropriate storage or handling of cell-associated vaccines can lead to a loss of titre of the vaccine virus, resulting in the targets not receiving a full dose, thereby decreasing the efficacy of protection. To stabilise the virus-infected host cells they are frozen in a cryoprotective medium, typically containing a (calf) serum and DMSO. Immediately before use, the vaccines are quickly thawed and diluted to the correct titre per dose. This is commonly done by reconstitution in a diluent that can be delivered with the vaccine, in a dilution of 1:25-1:100 of the infected cell-suspension. The diluent provides for the in-use stability during the time it takes to administer the vaccine to a group of target animals, typically 1-2 hours.

Considering the vast number of doses required every year of vaccines against Marek's disease and ILT, and especially in relation to the demanding production and logistics of these vaccines, it is highly desirable to retrieve as much as possible from their viral titre for the delivery to the target animals in need of such vaccination. Commonly the reconstitution in a standard diluent reduces titre loss to 0.4-0.6 Log 10 plaque forming units (pfu)/ml, during an in-use period of 2 hours at room temperature. However for some HVT vector vaccines, occasionally higher losses of viral titre were observed; these losses are then compensated by providing a higher starting titre.

It is therefore an object of the present invention to overcome a disadvantage in the prior art, and to accommodate to this need in the field by providing ways and means to improve the diluent used for the reconstitution of cell-associated alphaherpesvirus vaccines.

Surprisingly it was found that this object can be met, and consequently one or more disadvantages of the prior art can be overcome, by the use of an amended diluent for cells infected with a cell-associated alphaherpesvirus. The amended diluent has a much reduced amount of proteinaceous ingredient, as compared to the diluents normally used for this purpose in the field.

The use of this diluent provides for an improved in-use stability, whereby the loss of titre of even the most sensitive cell-associated alphaherpesvirus in dilution after thawing, can now be reduced to 0.4 Log 10 pfu/ml or less during 4 hours at room temperature after the reconstitution of the vaccine. This advantageous reduction of titre loss is of huge economic relevance to this sector of industry.

This was surprising, because it has been the common practice for over 40 years to use high amounts of a proteinaceous compound in the diluent for cell-associated alphaherpesvirus vaccines, such as of MDV or HVT, typically with 1.4-1.5% w/v of protein in the current commercial diluents.

Nevertheless the inventors found that the concentration of protein in the diluent could be significantly reduced, to below 0.5% w/v, and even down to zero, while providing excellent in-use stability.

This invention allows for a more complete use of the alphaherpesvirus vaccine virus provided, or alternatively it makes that less excess virus needs to be provided as compensation for losses.

The most significant advantages are reached in case the amended diluent is used in protein-free form: cost reduction—a protein hydrolysate is a relatively expensive ingredient; improved safety—reduced risk of introduction of extraneous agents; efficiency of production—averting the need to clean the production-line after each production run; and improved consistency of production—the new diluent no longer contains ill-defined bulk compounds, thereby providing a much improved controllability of ingredient quality and reproducibility of the end product. Further, the protein-free diluent is 'animal component free', and also 'chemically defined', which are important aspects of safety and consistency. Also, all ingredients of the diluent can be sterilised.

It is not known exactly how or why the protein content in the diluent can be so strongly reduced, without affecting its stabilising properties. Although the inventors do not want to be bound by any theory or model that might explain these findings, they speculate that it may be that the protein-component that was commonly used, was never actually entirely beneficial, but rather introduced variable negative effects, for example on the pH of the diluent. With a reduction, or even a removal of such disturbing effects a buffered solution with a sugar is then able to provide effective stabilisation of the virus-infected cells during the in-use period.

Therefore in one aspect the invention relates to the use of a diluent for the in-use stabilisation of cells infected with a cell-associated alphaherpesvirus, characterised in that the diluent comprises a sugar, a phosphate buffer and no more than about 0.7% w/v protein.

The use according to the invention of the diluent, serves to reconstitute the virus-infected cells after they are retrieved from frozen storage. The diluent assists in the recovery of the health of the infected cells, and sustains that health for several hours at room-temperature. The reconstituted infected cells in the diluent can then be administered to human or animal targets in need of such treatment.

The terms "in-use" refer to their common meaning as used in several regulatory guidelines such as the European Pharmacopoeia and the 9 CFR to refer to requirements on in-use stability and in-use shelf-life.

For the invention the in-use period is the period wherein the cells infected with a cell-associated alphaherpesvirus are comprised in the diluent of the invention. This period starts upon the admixing of the infected cells (typically from a thawed cell-suspension) and the diluent, and ends with the administration of the infected cells in the diluent to a target.

The "diluent" for the use according to the invention is an aqueous liquid. Because the diluent is intended for administration to human or animal targets, it will have to be prepared according to the proper standards of pharmaceutical manufacturing, for example to be sterile, and essentially free from pyrogens.

A virus is "cell-associated" if it remains to a greater or lesser extent within its host cell after its replication cycle is completed. Examples of cell-associated alphaherpesviruses are: varicella zoster virus, ILTV, MDV, and HVT.

A "sugar" for the invention is any compound from the group of water-soluble carbohydrates of relatively low molecular weight that typically have a sweet taste. The term "sugar" includes reducing sugars (such as fructose and maltose), non-reducing sugars (such as sucrose and trehalose), sugar alcohols (such as xylitol and sorbitol), sugar acids (such as gluconic acid and tartaric acid) and mixtures thereof. The term sugar also covers mono-, di-, or polysaccharides up to and including hexa-saccharides.

The term "comprises" (as well as variations such as "comprise", "comprising", and "comprised") as used herein, intends to refer to all elements, and in any possible combination conceivable for the invention, that are covered by or included in the text section, paragraph, claim, etc., in which this term is used, even if such elements or combinations are not explicitly recited; and not to the exclusion of any of such element(s) or combinations.

Thus any such text section, paragraph, claim, etc., can therefore also relate to one or more embodiment(s) wherein the term "comprises" (or its variants) is replaced by terms such as "consist of", "consisting of", or "consist essentially of".

The term "protein" refers to a molecule having 2 or more amino acids. A protein can be a native or a mature protein, a pre- or pro-protein, or a part of a protein. Inter alia: peptides, oligopeptides and polypeptides are included within the definition of protein. For the invention, the protein can be a pure, a purified, or an isolated protein, or can be a more or less crude preparation containing two or more different proteins of different types and sizes. Examples of a crude protein preparation are protein extracts or enzymatic digests or hydrolysates of a protein source. The protein source can be of animal or vegetable origin. Examples of common protein sources for preparation of extracts are bovine milk casein, animal hide, animal meat or tissue, yeast and soy.

For the invention the amount of protein in the diluent for the use according to the invention refers to the total amount of protein in the diluent, and is determined as "% w/v", i.e. a percentage in weight-per-volume. This percentage is to be determined on the basis of the volume of the diluent itself, and thus not on the basis of the final vaccine composition ready for administration, that is prepared by admixing the infected cells with the diluent.

Similarly, the amount of protein in the diluent for the use according to the invention is determined for the diluent itself, before it is combined with the infected cells. This because such infected cells will commonly be contained in a rich freezing medium, which will comprise a certain amount of protein.

Without prejudice to the details and concentrations of the composition of the diluent for the use according to the invention as described herein, the diluent may also be produced, marketed, or stored in a more concentrated form, e.g. concentrated 2 or more times. This concentrated form of the diluent is then diluted to its final 1× concentration before the use according to the invention. Such concentration of the diluent is advantageous for example for logistic reasons, to reduce volume and save costs for packaging and transportation.

Details of preferred embodiments and of further aspects of the invention will be described below.

For the invention "about" indicates that a number can vary between ±10% around its indicated value. Preferably "about" means ±9% around its value, more preferably "about" means ±8, 7, 6, 5, 4, 3, 2% around its value, or even "about" means ±1% around its value, in that order of preference.

As described, it is highly advantageous to have little to none protein in the diluent for the use according to the invention.

Therefore in an embodiment of the use according to the invention, the diluent comprises no more than about 0.45% w/v of protein. Preferably the diluent comprises no more than about 0.6, 0.5, 0.45, 0.4, 0.35, 0.3, 0.25, 0.2, 0.15, 0.1, 0.05, 0.03, 0.01% w/v of protein, in that order of preference.

Therefore in a preferred embodiment of the use according to the invention, the diluent comprises no more than about 0.1% w/v protein.

In a more preferred embodiment of the use according to the invention, the diluent is protein-free.

Being "protein-free" effectively means that no proteinaceous compound is comprised in the diluent; i.e. it is substantially free of protein, and no protein, hydrolysate, etc. is added to or used in the preparation of the diluent. However this does not rule out the presence of trace amounts of protein in the diluent, which might be detectable using advanced or highly sensitive methods and equipment. For the invention the diluent is protein-free if it contains no more than 0.0001% w/v of protein, i.e. no more than 1 mg protein per litre of the diluent in its 1× concentration.

For the invention, the indication of a range, either one- or two-sided, is intended to include the stated end-point(s).

As described, the diluent for the use according to the invention is of special advantage for use with cells infected with a cell-associated alphaherpesvirus.

In an embodiment of the use according to the invention, the cell-associated alphaherpesvirus is of a genus selected from Mardivirus and Iltovirus.

Preferably, the cell-associated alphaherpesvirus is selected from: varicella zoster virus, ILTV, MDV, and HVT.

In a more preferred embodiment of the use according to the invention, the cell-associated alphaherpesvirus is selected from: MDV and HVT.

In an embodiment of the use according to the invention, the cell-associated alphaherpesvirus is herpesvirus of turkeys.

An 'alphaherpesvirus' refers to a virus of the subfamily alphaherpesvirinae, having the characterising features of its taxonomic group-members such as the morphologic, genomic, and biochemical characteristics, as well as the biological characteristics such as physiologic, immunologic, or pathologic behaviour. The same applies for a reference to a genus such as Mardivirus or Iltovirus, as well as to a reference to names of individual virus species.

As is known in the field, the classification of a micro-organism in a particular taxonomic group is based on a combination of such features. The invention therefore also includes species of alphaherpesvirus that are sub-classified therefrom in any way, for instance as a subspecies, strain, isolate, genotype, variant, subtype or subgroup and the like.

Further, it will be apparent to a person skilled in the field of the invention that while a particular subfamily, genus or species of alphaherpesvirus for the invention may currently be assigned to that group, however that is a taxonomic classification that could change in time as new insights can lead to reclassification into a new or different taxonomic group. However, as this does not change the micro-organism itself, or its antigenic repertoire, but only it's scientific name or classification, such re-classified micro-organisms remain within the scope of the invention.

Samples of cell-associated alphaherpesvirus for use in the invention can be obtained from a variety of sources, e.g. as field isolate from a human, or from an animal in the wild or on a farm, or from various laboratories, (depository) institutions, or (veterinary) universities.

The host cells that are infected with the cell-associated alphaherpesvirus for the invention are preferably of avian origin, as such cells have been found to provide optimal conditions for replication of the cell-associated alphaherpesviruses that are infective to avians.

For the invention, "avian" refers to an organism of the taxonomical class Ayes. Preferably the donor animal for the host cells is an avian of agricultural relevance, such as: chicken, turkey, duck, goose, partridge, peacock, quail, pigeon, pheasant, guinea fowl, or ostrich.

More preferred are avians selected from the group consisting of: chicken, turkey, duck and goose. Even more preferred avian donor organism for the host cells is chicken.

In an embodiment of the use according to the invention, the infected cells are avian fibroblasts.

Methods to characterise cells as being of avian and of fibroblastic origin exist by several well-known techniques such as karyotyping, and detection of specific markers expressed by the cells.

The avian cells for the invention that are infected with the cell-associated alphaherpesvirus, can be primary cells prepared from an avian animal or its parts. Preferably the avian cells are chicken embryo fibroblasts (CEFs).

Alternatively, and preferably, the avian cells are secondary cells, i.e. are from a cell-line.

Even more preferred, the avian cells infected with cell-associated alphaherpesvirus for the invention, are from a cell-line of immortalised CEFs as described in WO 2016/087560.

In order to reconstitute and stabilise the infected cells for the use according to the invention, the diluent for the use according to the invention preferably has a pH that is at or near the optimal pH for those cells. For cells that can be infected with MDV, HVT or ILTV, this means the pH is preferably in the range of about 7.0 to about 7.8.

Therefore in an embodiment of the use according to the invention, the diluent has a pH in the range from about 7.0 to about 7.8.

More preferably the diluent for the use according to the invention has a pH in the range from about 7.1 to about 7.7; more preferably from about 7.1 to about 7.6.

In an even more preferred embodiment, the diluent for the use according to the invention has a pH in the range from about 7.1 to about 7.5.

To establish and maintain the pH of the diluent for the use according to the invention at the desired level, the diluent comprises a phosphate buffer.

In a preferred embodiment of the use according to the invention, the phosphate buffer in the diluent is a so-called Gomori buffer, consisting of a mixture of a monobasic dihydrogen phosphate and a dibasic monohydrogen phosphate. The phosphate compounds can be derived from any common salt, such as for example a sodium-, or a potassium salt, whereby both can be the same type of salt or can be different. These phosphate compounds have several synonyms, for example: $Na_2HPO_4$ is called: sodium phosphate dibasic or disodium hydrogen phosphate. Equally e.g. $KH_2PO_4$ is called: monopotassium phosphate, or potassium dihydrogen phosphate.

In a preferred embodiment of the use according to the invention the phosphate buffer in the diluent is comprised of $Na_2HPO_4$ and $KH_2PO_4$.

Preferably the combined phosphate buffer is at a concentration between about 5 and 25 mM; more preferably the combined phosphate buffer is at a concentration of about 10 mM.

Preferably the $Na_2HPO_4$ is at a concentration between about 5 and about 9 mM, and the $KH_2PO_4$ is at between about 1 and about 4 mM; preferably the $Na_2HPO_4$ is at about 8 mM, and the $KH_2PO_4$ is at about 2.5 mM.

To stabilise the cells infected with a cell-associated alphaherpesvirus of the invention, the diluent for the use according to the invention comprises a sugar.

In an embodiment of the use according to the invention, the sugar in the diluent is at least one selected from the group consisting of: glucose, lactose, sucrose, maltose, trehalose, dextrose, sorbitol and mannitol.

In a preferred embodiment of the use according to the invention, the sugar in the diluent is sucrose.

In an embodiment of the use according to the invention, the sugar in the diluent is at a concentration between about 50 and about 500 mM.

In a preferred embodiment, the sugar is at a concentration between about 75 and 400 mM; more preferably between about 100 and 350 mM.

Next to improving the stabilising properties of the diluent, optimising the amount of sugar is also a way to adapt the osmolarity of the diluent. This is of relevance to prevent tissue irritation upon parenteral administration to the vaccine target, as well as to assure optimal in-use stability of the infected cells of the invention.

In an embodiment of the use according to the invention, the osmolarity of the diluent for the invention is not specifically controlled; the osmolarity is generally between about 150 and 350 mili Osmoles/kilogram (mOsm/kg).

In a preferred embodiment, the osmolarity of the diluent for the invention is controlled to a more physiological range, and is preferably of isotonic osmolarity.

This means the diluent is preferably at an osmolarity between about 250 and 300 mOsm/kg; more preferably between about 280 and about 290 mOsm/kg.

To provide the diluent for the use according to the invention with such osmolarity, the ionic content can be adapted, for example by including salts such as sodiumchloride and/or potassiumchloride, or by increasing the concentration of sucrose.

In a preferred embodiment of the use according to the invention, the concentration of potassium in the diluent is at or near the physiologic levels of a vertebrate bodies' extracellular environment; meaning that potassium is at a concentration between about 3 and about 5 mM.

The level of sodium can then be varied to compensate the total osmolarity, and can be between about 50 and 250 mM.

A diluent for the use according to the invention may comprise a preservative, such as thimerosal, merthiolate, phenolic compounds, and/or gentamicin. Preferably no preservative is employed.

The diluent for the use according to the invention, may incorporate an amount of magnesium ions. The magnesium ions were found to contribute to the recovery of the health of infected host cells after thawing, resulting in a reduction of the loss of titre of the cell-associated alphaherpesvirus. Remarkably this effect appeared to be specific for magnesium, as another bivalent cation, calcium, was found not to have a beneficial effect.

In an embodiment of the use according to the invention, the diluent comprises magnesium ions at a concentration between about 0.1 and about 10 milimoles per litre (mM).

With regard to the range of magnesium ions in the diluent for the use according to the invention, the upper border is limited for practical reasons, as too high amounts of magnesium may cause the generation of precipitates upon heat sterilisation of the diluent, for example in combination with the phosphate compound(s) in the diluent. The lower border is limited by still having the effect of stabilising the infected cells.

In a preferred embodiment of the use according to the invention, the diluent comprises magnesium ions at a concentration between about 0.2 and about 9 mM. More preferably between 0.3 and 8 mM, between 0.4 and 5 mM; between 0.5 and 2.5 mM; between 0.6 and 2 mM; between 0.7 and 1.5 mM; or even between 0.75 and 1.25 mM, in that order of preference.

In an even more preferred embodiment of the use according to the invention, the diluent comprises magnesium ions at a concentration of about 1 mM.

The diluent for the use according to the invention, may incorporate an amount of citrate. The citrate was found to contribute to the recovery of the health of infected host cells after thawing, resulting in a reduction of the loss of titre of the cell-associated alphaherpesvirus. This effect can be due to a use of the citrate as a metabolite for the virus-infected cells, and/or by an effect as an anti-oxidant. Resulting titres after 4 hours at 25° C. were higher by up to 0.5 pfu/ml when citrate was added to the diluent.

Therefore in an embodiment of the use according to the invention, the diluent comprises citrate at a concentration between about 0.1 and about 10 milimoles per litre (mM).

The higher concentration of citrate may have an effect on the pH of the diluent, which can be compensated by adapting the buffer strength.

In a preferred embodiment of the use according to the invention, the diluent comprises citrate at a concentration between about 0.2 and about 9 mM. More preferably between 0.3 and 8 mM, between 0.4 and 5 mM; between 0.5 and 2.5 mM; between 0.6 and 2 mM; between 0.7 and 1.5 mM; or even between 0.75 and 1.25 mM, in that order of preference.

In an even more preferred embodiment of the use according to the invention, the diluent comprises citrate at a concentration of about 1 mM.

The diluent according to the invention may also comprise a pH indicator, to provide a visual check for any microbiological contamination. The pH indicator can be any pharmaceutically acceptable indicator, effective in the range of pH 5-8; preferred pH indicator is phenolsulfonphtalein, at an amount of between about 0.005-0.05 mg/ml.

More preferred, the phenolsulfonphtalein is comprised at about 0.01-0.02 mg/ml.

In an embodiment of the use according to the invention, for the diluent one or more of the conditions apply, selected from the group consisting of:

- the diluent comprises no more than about 0.6, 0.5, 0.45, 0.4, 0.35, 0.3, 0.25, 0.2, 0.15, 0.1, 0.05, 0.03, 0.01% w/v of protein, in that order of preference;
- the diluent is protein free;
- in the diluent the cell-associated alphaherpesvirus is of a genus selected from Mardivirus and Iltovirus;
- in the diluent the cell-associated alphaherpesvirus is selected from: varicella zoster virus, ILTV, MDV, and HVT; preferably is selected from: MDV and HVT;
- the cells that are infected with the cell-associated alphaherpesvirus for the invention are preferably of avian origin; preferably the donor animal for the host cells is an avian of agricultural relevance, such as: chicken, turkey, duck, goose, partridge, peacock, quail, pigeon, pheasant, guinea fowl, or ostrich; more preferred are avians selected from the group consisting of: chicken, turkey, duck and goose. Even more preferred avian donor organism for the host cells is chicken.
- the infected cells are avian fibroblasts; preferably, the avian cells are secondary cells; more preferred the avian fibroblast cells infected with cell-associated alphaherpesvirus for the invention, are from a cell-line of immortalised CEF as described in WO 2016/087560;
- the diluent has a pH in the range from about 7.0 to about 7.8; preferably from about 7.1 to about 7.7; from about 7.1 to about 7.6; more preferably from about 7.1 to about 7.5;
- in the diluent the phosphate buffer is a so-called Gomori buffer, consisting of a mixture of a monobasic dihydrogen phosphate and a dibasic monohydrogen phosphate;
- the phosphate buffer of the diluent is comprised of $Na_2HPO_4$ and $KH_2PO_4$; preferably the $Na_2HPO_4$ is at a concentration of between about 5 and about 9 mM, and the $KH_2PO_4$ is between about 1 and about 4 mM; preferably the combined phosphate buffer is about 10 mM; preferably the $Na_2HPO_4$ is at a concentration of about 8 mM, and the $KH_2PO_4$ is at about 2.5 mM;
- in the diluent the sugar is at least one selected from the group consisting of: glucose, lactose, sucrose, maltose, trehalose, dextrose, sorbitol and mannitol; in a preferred embodiment, the sugar is sucrose;
- in the diluent, the sugar is at a concentration between about 50 and about 500 mM; between about 75 and 400 mM; or even between about 100 and 350 mM;
- the diluent is at an osmolarity between about 150 and 350 mOsm/kg; more preferably between about 250 and 300; or even between about 280 and about 290 mOsm/kg;
- in the diluent potassium is at about 3-5 mM, and sodium is between 50 and 250 mM;
- the diluent comprises magnesium ions at a concentration between about 0.1 and about 10 milimoles per litre (mM), between 0.2 and 9 mM, between 0.3 and 8 mM, between 0.4 and 5 mM; between 0.5 and 2.5 mM; between 0.6 and 2 mM; between 0.7 and 1.5 mM; or even between 0.75 and 1.25 mM, in that order of preference;
- the diluent comprises magnesium ions at about 1 mM;
- the diluent comprises citrate at a concentration between about 0.1 and about 10 mM, between 0.2 and 9 mM, between 0.3 and 8 mM, between 0.4 and 5 mM; between 0.5 and 2.5 mM; between 0.6 and 2 mM; between 0.7 and 1.5 mM; or even between 0.75 and 1.25 mM, in that order of preference;
- the diluent comprises citrate at about 1 mM; and
- the diluent comprises a pH indicator that is pharmaceutically acceptable, and is effective in the range of pH 5-8; preferred pH indicator is phenolsulfonphtalein, at an amount of between about 0.005-0.05 mg/ml; more preferred, the phenolsulfonphtalein is comprised at about 0.01-0.02 mg/ml.

In an embodiment of the use according to the invention, the diluent is protein free; is for the in-use stabilisation of cells infected with a cell-associated alphaherpesvirus, selected from MDV and HVT; has a pH in the range from about 7.0-7.5; comprises in the phosphate buffer $KH_2PO_4$ at between about 1 and about 4 mM, and $Na_2HPO_4$ at a concentration of between about 5 and about 9 mM; the sugar is sucrose, and is at between about 100 and 350 mM; sodium is at between about 50 and 250 mM; and phenolsulfonphtalein is comprised at about 0.01-0.02 mg/ml.

As described, the diluent for the use according to the invention allows for an improved in-use stability of reconstituted cells infected with a cell-associated alphaherpesvirus. Further, the use of the adapted diluent has a number of practical and economic advantages.

Therefore in a further aspect, the invention relates to a process for the in-use stabilisation of cells infected with a cell-associated alphaherpesvirus, the process comprising the step of admixing a suspension of said infected cells with the diluent for the use according to the invention.

The admixing is done using common tools and methods, typically as recommended by the manufacturer of the infected cell-suspension, for example as described in a leaflet accompanying the cell-suspension product, and/or a leaflet accompanying the diluent.

In an example of the process according to the invention a suspension of the infected cells in freezing-medium is taken from its frozen storage, is quickly thawed, and is then combined with the diluent. In a more detailed example: an ampule of about 2 ml of a suspension of cells infected with a cell-associated alphaherpesvirus, having e.g. 1000 vaccine doses is thawed in a waterbath; the contents of the ampule are taken up into about 200 ml of diluent, which is a dilution of about 1:100 of the infected cell-suspension. The admixture of cells in diluent is administered at 0.2 ml per target subcutaneously or intramuscularly. Alternatively when the administration is to be given by the in ovo route, this inoculum is taken up into 50 ml, which is a dilution of about 1:25 of the infected cell-suspension, for a dose-volume of 50 µl per egg.

At the moment of the admixing the diluent can be at room temperature, or can be cooled at 2-8° C. Preferably the diluent is at room temperature at the moment of the admixing, i.e. at a temperature between about 15 and about 30° C.; or even between about 20 and about 25° C. This was found to provide the best survival of viral titre of the cell-associated alphaherpesvirus.

As described, both the use and the process according to the invention, are particularly suited for the preparation of a vaccine against infection or disease caused by the cell-associated alphaherpesvirus of the invention.

Therefore a further aspect of the invention is a vaccine against cell-associated alphaherpesvirus, the vaccine comprising cells infected with said virus, characterised in that the cells are suspended in the diluent for the use according to the invention.

For the invention, the 'vaccine' is the admixture of cells infected with cell-associated alphaherpesvirus, and the diluent for the use according to the invention. In practice this will be a dilution of a suspension of infected cells as provided by a vaccine manufacturer.

The vaccine according to the invention is intended for administration to suitable human or animal targets, to induce active immunisation in order to reduce infection and/or of signs of disease caused by the cell-associated alphaherpesvirus. Such reduction of infection refers to preventing or reducing the establishment or the proliferation of a productive infection by the alphaherpesvirus in a target animal. This is achieved for example by reducing the viral load in the target or shortening the duration of the viral replication. In turn this leads in the target animal to a reduction of the number, the intensity, or the severity of lesions and consequential clinical signs of disease caused by the viral infection. Such a vaccine is colloquially referred to as a: vaccine 'against' the alphaherpesvirus, or as an 'alphaherpesvirus vaccine'.

In an embodiment of the vaccine according to the invention, the vaccine is for avians, and the cell-associated alphaherpesvirus is selected from ILTV, MDV, and HVT.

In an embodiment the MDV is a vaccine strain selected from MDV1 and MDV2.

More preferably the MDV is a strain selected from: RB1B, 814, CVI-988 Rispens, and SB1.

In an embodiment the HVT is a strain selected from: PB1 and FC-126.

In a preferred embodiment of the vaccine according to the invention the HVT is a recombinant HVT which expresses one or more heterologous antigen(s). Examples of recombinant HVT for use in the vaccine according to the invention are as described in: WO 2016/102647 and WO 2013/057236.

In an even more preferred embodiment of the vaccine according to the invention, the cell-associated alphaherpesvirus is a recombinant HVT or MDV, expressing one or more heterologous antigens derived from: ILTV, NDV, Gumboro disease, MDV and Avian influenza virus.

The determination of the effectiveness of a vaccine according to the invention, is well within the skills of the routine practitioner, and can be done for instance by monitoring the immunological response following vaccination or by testing the appearance of clinical symptoms or mortality after a challenge infection, e.g. by monitoring the targets' signs of disease, clinical scores, serological parameters, or by re-isolation of the challenge pathogen, and comparing these results to a vaccination-challenge response seen in mock vaccinated animals. To assess vaccine efficacy against Marek's disease, challenge survival is a convenient measurement, along with egg-production, and feed-conversion.

A further advantageous effect of the vaccine according to the invention, is the prevention or reduction of the spread of the alphaherpesvirus within an animal herd or a population, and/or within a geographical area. Consequently, the use of a vaccine according to the invention leads to a reduction of the prevalence of the alphaherpesvirus.

Therefore in a preferred embodiment the vaccine according to the invention is effective as an aid in the prevention of alphaherpesvirus viremia, and/or as an aid in the prevention of the shedding of the alphaherpesvirus by infected humans or animals.

In another preferred embodiment of the vaccine according to the invention, the vaccine is for reducing the prevalence of the alphaherpesvirus in an avian population and/or in a geographical area.

The vaccine according to the invention in principle can be given to human or animal targets by different routes of application, and at different points in their lifetime.

However, because an infection with MDV or ILTV can be established already at very young age, it is advantageous to apply the vaccine according to the invention as early as possible. Therefore the vaccine according to the invention can be applied at the day of hatch ("day 1"), or in ovo, e.g. at 18 days ED.

Therefore, in an embodiment the vaccine according to the invention is administered in ovo.

Equipment for automated injection of a vaccine into an egg at industrial scale, is available commercially, e.g. the INOVOJECT® (Embrex BioDevices). This provides the earliest possible protection, while minimising labour cost. Different in ovo inoculation routes are known, such as into the yolk sac, the embryo, or the allantoic fluid cavity; these can be optimised as required. Preferably in ovo inoculation is performed such that the needle actually touches the embryo.

In an embodiment, the vaccine according to the invention is administered by parenteral route; preferably by intramuscular- or subcutaneous route.

For the vaccine according to the invention, the preferred dose of virus inoculum is between $1\times10^1$ and $1\times10^5$ pfu of the cell-associated alphaherpesvirus per target-dose; more preferably between $1\times10^2$ and $1\times10^4$ pfu/dose; even more preferably between 500 and 5000 pfu/dose; most preferably between about 1000 and about 3000 pfu/dose.

The volume per target-dose of the vaccine according to the invention can be optimised according to the intended route of application: in ovo inoculation is commonly applied with a dose of between about 0.01 and about 0.5 ml/egg, and parenteral injection is commonly done with a dose of between about 0.1 and about 1 ml/target.

Determination of what is an immunologically effective amount of the vaccine according to the invention, or the optimisation of the vaccine's volume per dose, are both well within the capabilities of the skilled artisan.

The vaccine according to the invention may comprise a further immunologically active component.

In an embodiment the further immunologically active component is a cytokine or an immunostimulatory oligodeoxynucleotide.

The immunostimulatory oligodeoxynucleotide is preferably an immunostimulatory non-methylated CpG-containing oligodeoxynucleotide (INO), as described in WO 2015/011261.

A preferred INO is an avian Toll-like receptor (TLR) 21 agonist, such as described in WO 2012/089.800 (X4 family), in WO 2012/160.183 (X43 family), or in WO 2012/160.184 (X23 family).

In an embodiment of the vaccine according to the invention, the further immunologically active component is an antigen which is derived from a micro-organism pathogenic to an avian. This can be 'derived' in any suitable way, for instance as a 'live' attenuated, an inactivated, or a subunit antigen from that micro-organism pathogenic to an avian.

A preferred further immunologically active component is one or more live attenuated vaccine strain(s) selected from: Newcastle disease virus strain C2; infectious bursal disease virus strain D78, PBG98, Cu-1, ST-12 or 89-03; and Eimeria.

A vaccine according to the invention can be used either as a prophylactic- or as a therapeutic treatment, or both, as it interferes both with the establishment and with the progression of an infection by a cell-associated alphaherpesvirus or its signs of disease.

The regime for the administration of the vaccine according to the invention preferably is integrated into existing vaccination schedules of other vaccines that the target may require, in order to reduce stress to the target and/or to reduce labour costs. These other vaccines can be administered in a simultaneous, concurrent or sequential fashion, in a manner compatible with their registered use.

Preferably the vaccine according to the invention is only administered once, as a single-shot.

In a further aspect the invention relates to a process for the preparation of a vaccine according to the invention, the process comprising the step of admixing cells infected with a cell-associated alphaherpesvirus, and the diluent for the use according to the invention.

The vaccine according to the invention can be prepared from a suspension of cells infected with a cell-associated alphaherpesvirus for the invention and the diluent for the use according to the invention, by methods as described herein, which are readily applicable by a person skilled in the art.

General techniques and considerations that apply to the preparation of vaccines are well known in the art and are described for instance in governmental regulations and in handbooks such as: "Remington: the science and practice of pharmacy" (2000, Lippincot, USA, ISBN: 683306472), and: "Veterinary vaccinology" (P. Pastoret et al. ed., 1997, Elsevier, Amsterdam, ISBN 0444819681).

The invention will now be further described by the following, non-limiting, examples.

EXAMPLES

Example 1: Outline of Stability Assays

The base of the diluent for the use according to the invention is formed by phosphate buffer and sucrose.

The phosphate buffer is used at 10 mM, and is set at a certain pH level by selecting the composition of the two phosphates. For example for a pH of 7.3 the diluent contained: 0.324 mg/ml of $KH_2PO_4$, and 1.356 mg/ml of $Na_2HPO_4.2H_2O$.

Sucrose was used at 50 mg/ml (i.e. 150 mM), some diluent samples tested had a higher sucrose content of 92.5 mg/ml (i.e. 270 mM).

Phenolsulfonphtalein was used at 0.01 or 0.02 mg/ml.

To some diluent samples tested magnesium was added at 1 mM of $MgCl_2$.

In some diluent samples tested $CaCl_2$) was added to 0.133 mg/ml.

In some diluent samples tested NaCitrate was added to 1 mM.

In some diluent samples tested, peptone inclusion was used: NZ-amine AS, from Kerry Inc., pancreatic digest of casein, used at 1-14 mg/ml.

Positive control for the stability studies was complete CEF culture medium comprising 1% v/v newborn calf serum and an antibiotics mixture.

In-use stability incubations were performed by incubating samples of HVT-infected CEFs at room temperature (20-25° C.) for up to 4 hours. Next the samples were immediately titrated on overnight dishes with CEFs.

The virus used for these stability assays was a recombinant HVT vector virus, construct HVP360, as described in WO 2016/102647. This comprises a double insert of heterologous genes: the NDV-F gene and the IBDV-VP2 gene. This recombinant virus had a reduced in-use stability as compared to non-recombinant HVT or MDV, in standard MDV diluent comprising 1.4% w/v peptone.

Titration assays were standard: CEFs from 10 day old chicken embryos were prepared and seeded on 6 cm dishes. After attachment overnight (38° C., 5% $CO_2$), next day, the dished were inoculated with dilutions of incubated samples from the stability assays. The dishes were incubated again until cpe became visible, usually after about 3 days. Titres were read by scoring cpe, preferably by using immunofluorescense by way of an antibody against HVT virus.

Example 2: Tests of Amounts of Peptone in the Diluent

In an initial experiment, the effect of peptone amount was tested. Samples of recombinant HVP360-infected CEFs were incubated for 4 hours at room temperature in diluent compositions comprising different amounts of NZ-amine. The diluent used in these experiments had a pH of 7.4, and included magnesium- and calcium ions. One series of samples were incubated in diluent plus 1% v/v NCS, to mimic cell-culture medium.

After incubations, samples were titrated on CEFs, in triplo, and the difference between titre before (t=0 hours) and after incubation (t=4 hours) was calculated as the 'delta'. Standard deviation of titres was typically about 0.1. All titres are in 10 Log plaque forming units per ml.

TABLE 1

Effect of different amounts of peptone on in-use stability of rec. HVT in CEF

| Diluent | added | added 2 | Titre in 10Log PFU/ml | |
| --- | --- | --- | --- | --- |
| | | | t = 0 hr | delta @ t = 4 hr |
| PB, pH 7.4, sucrose | Mg, Ca | NZamine, 1 mg/ml | 6.14 | −0.18 |
| | | NZamine, 7 mg/ml | 6.17 | −0.29 |
| | | NZamine, 14 mg/ml | 6.18 | −0.56 |
| | | 1% NCS | 6.18 | −0.11 |

PB = phosphate buffer

As was clear from these results, the presence of peptone could not mimic the effect of NCS, on the contrary: where NCS gave the smallest titre loss of all samples tested, the presence of peptone in the amount of the standard MDV diluent, 14 mg/ml (1.4% w/v), had the most negative effect: 7 mg/ml (0.7% w/v) was already better, and best in this experiment was the use of diluent with 1 mg/ml peptone (0.1% w/v). In conclusion: less peptone gave less titre loss.

Example 3: Tests of Low Amounts of Peptone

A follow-up experiment was done to investigate the use of low amounts of peptone. This time the diluent did not contain magnesium or calcium, but different pH values were tested. Titrations were done in duplo.

TABLE 2

Effect of low amounts of peptone on in-use stability of rec. HVT in CEF

| Diluent | pH | added | Titre in 10Log PFU/ml t = 0 hr | delta @ t = 4 hr |
|---|---|---|---|---|
| PB, sucrose | 7.2 | — | 5.6 | −0.23 |
|  | 7.4 |  | 5.5 | −0.14 |
|  | 7.2 | NZamine, 1 mg/ml | 5.5 | −0.47 |
|  | 7.4 |  | 5.5 | −0.34 |
|  | 7.2 | NZamine, 3 mg/ml | 5.5 | −0.62 |
|  | 7.4 |  | 5.6 | −0.57 |
| Nobilis Diluent CA |  |  | 5.4 | −1.05 |
| Culture medium + 1% NCS |  |  | 5.6 | −0.02 |

Several conclusions could be drawn from these results:
worst losses (highest delta after 4 hrs. at 25° C.) were found for this recombinant HVT construct when kept in a standard commercial MDV diluent (containing 14 mg/ml peptone)
least losses were found for complete culture medium
a basic diluent of phosphate buffer with sucrose was quite effective at reducing titre loss of recombinant HVT in CEF, for up to 4 hours at room temperature
magnesium and calcium were not required
diluent at pH 7.4 was more effective at reducing losses than diluent at pH 7.2
the lower the amount of peptone, the better, with the protein-free diluent as most effective.

Example 4: Further Variations of the Diluent

In continuation of the experiment in Example 3 above, further variations of the diluent compositions were tested: addition of 0.1 mg/ml magnesium; correction to iso-osmotic value by adding salts: either 3.16 mg/ml NaCl; or the combination of 0.17 mg/ml KCl and 2.92 mg/ml NaCl. Alternatively iso-osmotic values were produced by increasing sucrose to 92.5 mg/ml, and no further salts.
Also inclusion of 1 mM citrate in the diluent was tested.
In-use stability results of these different compositions showed that:
a low amount of magnesium can provide some further reduction of titre loss; a similar further reduction could be reached using increased sucrose concentration.
the different ways to create iso-osmotic values had similar effects
the inclusion of 1 mM citrate in the diluent, next to phosphate buffer and sucrose, enhanced the in-use stability of rec. HVT virus.

Example 5: Animal Trial

To confirm that the cell-associated alphaherpesvirus was still effective as a vaccine after in-use stabilisation using the diluent according to the invention, animal trials are in preparation to test for protective effect against a challenge infection with MDV, or with NDV or IBDV.
The basic set-up of the experiments will be a division over several test groups with appropriate controls.
For a test of the protective effect against a challenge with MDV, it is common to apply the MDV challenge by way of shedder birds.
Protection against NDV or IBDV, will be tested using appropriate virulent virus from those viral species.

For a shedder trial, typically some 1140 fertilised chicken eggs will be used; about 240 of those will be used to generate birds that will serve as shedders. The rest will be divided over a number of test groups and two control groups: one receiving a control vaccination, and one receiving no vaccination.
A brief outline of the planned experiments is as follows:
General Protocol
A 2-4 hr in-use stability incubation will be applied to CEFs infected with a rec. HVT, whereby the cells are taken up into a diluent for the invention.
Vaccine viruses will be titrated prior to the start of the study to establish dilution for target doses.
Chickens will be obtained as 200 embryonated eggs at day 14 of embryo development (ED), and 900 unset, embryonated eggs (ED 1).
Eggs will be sorted and set according to:
240 (ED 14) for shedder treatment
150 (ED 1) for unvaccinated contacts
750 (ED 1) for vaccinate treatments; 125 to be in ovo vaccinated at ED 18
At ED 18, eggs for shedders will be candelled and placed in hatching trays.
At hatch, shedder chickens will be eyedrop vaccinated against Newcastle disease and infectious bronchitis, neck-tagged and inoculated intra-abdominally with 200-400 PFU of virulent MDV serotype 1 and placed at 50 per pen.
Birds will be provided food and water ad libitum and will be monitored and documented daily.
On ED 18 for control and vaccinates, eggs will be divided over the treatment groups, vaccinated in ovo, and placed in hatching trays. All vaccines used will be back-titrated.
At hatch, unvaccinated contacts and vaccinates will receive NDV/IBV eyedrop vaccine, will be neck-tagged and placed in contact with shedders.
Birds will be provided food and water ad libitum and will be monitored and documented daily.
At day 42 for the shedder birds, they will be euthanized and scored for MDV related lesions.
At day 29 post-placement, all unvaccinated contacts and vaccinates will receive a booster vaccine for NDV and IBV, by spray.
At day 49 post-placement, all remaining birds will be euthanized and scored for MDV related lesions.
Scoring of Chickens
All mortality, clinical signs (paralysis, torticollis, red-leg), and lesions will be recorded.
All lesions at termination (necropsy) will be recorded.
Data will be reported as % affected by MDV, treatment survival curve, and protective index
Protective Index
Protective indices (PI) will be based on Witter method:

PI=(% MD in unvaccinated)−(% MD in vaccinated)/(% MD in unvaccinated)×100

MD=signs of Marek's disease
Housing:
Birds will be housed in a single broiler house divided into 4 pens with automatic feeders and nipple waterers, with single radiant heating and air-handling systems.
Monitoring
Birds will be monitored daily for overall health, food, air circulation and water. Any culls or birds found dead, after two weeks post-placement, will be necropsied and lesions recorded. Birds succumbing during the first two weeks of life will be considered as "non-specific" mortality.

Duration

Experiment duration will be 63 days. Shedders will be placed 2 weeks prior to the vaccinates and will be co-housed for 28 days. Vaccinates/contacts will be kept for 7 weeks (49 days).

Example 6: Results of the Animal Experiment of Example 5

The vaccination-challenge experiment described in Example 5 was performed in the middle of 2018. Unfortunately a technical failure in the climate-handling equipment of the animal facility caused a massive heat-stress event for the birds in the different treatment groups. This caused a large number of the birds to die, and the remaining ones to have severely disrupted immune responses, which did not allow a meaningfull analysis of the data. A re-run of the experiment is now being planned.

Example 7: In-Use Stability Testing of Further Cell-Associated Alphaherpesviruses Preferred Diluent The preferred composition of the diluent for use in the stabilisation according to the invention was used for determining the in-use stability of cells infected with further cell-associated alphaherpesviruses, both from commercial vaccines and from laboratory strains.

The preferred version of the invention diluent is protein free, and has pH 7.1 after preparation, which shifts to 7.0 after heat sterilisation.

TABLE 3

Composition of preferred invention diluent

|  |  | g/l | mM |
|---|---|---|---|
| phosphate buffer | $KH_2PO_4$ | 0.451 | 3.3 |
|  | $Na_2HPO_4$ | 1.19 | 6.7 |
| sugar | sucrose | 50 | 146 |
| sodium | sodium-chloride | 3.16 | 54 |
| pH indicator | phenolsulfonphtalein | 0.01 | 0.03 |
| water for injection | — | To 1 litre | — |

Vaccines Tested

The various viruses tested are listed in Table 4. Virus was thawed from cold storage (−140° C.) and diluted in either the standard diluent Nobilis™ CA diluent, or in the preferred diluent for the invention. Dilutions for titrations were prepared as indicated in Table 4, and the t=0 samples for virus titration were titrated on plated CEF cells immediately. After 4 hours storage of the dilution at room temperature (about 21° C.), the dilutions were sampled again for titration on CEF to determine the end point of the in-use stability.

TABLE 4

Overview of experimental conditions of in-use stability testing of MDV viruses

| Test sample | type | dilution 1:x | no. replicates |
|---|---|---|---|
| Nobilis ® Rismavac | MDV1 | 80.000 | 2 |
| Innovax ® ILT | HVT + 2 inserts | 100.000 | 2 |
| Innovax ® ND | HVT + 1 insert | 500 | 4 |
| Innovax ® ND-IBD | HVT + 2 inserts | 75.000 | 6 |
| SB1 | MDV2 | 1.000 | 4 |
| FC126 | HVT | 40.000 | 4 |

Virus Titrations

Petri dishes (diameter 6 cm) were seeded with CEFs at a density of $1.1×10^5$ cells/cm$^2$ in 4 ml culture medium with antibiotics. These dishes were incubated overnight at 38° C. and 5% $CO_2$. After about 24 hours the CEF cells had reached a confluence of approximately 80%. 100 µl of each of the samples taken in the stability test was added to the dishes; the number of replicates is indicated in Table 4. Dishes were incubated for a further 3-4 days until virus plaques were visible.

IFT

Plaques on the dishes were visualised using immuno-fluorescence assays. At the time plaques became clearly visible, the cells on the dishes were fixated using cold (−20° C.) 96% ethanol for 3-5 minutes. Subsequently, dishes were washed three times using standard wash buffer. 3 types of monoclonal antibodies were used as first antibody, a specific one for each of the virus types tested here: HVT, MDV1, or MDV2. The monoclonal antibodies were diluted to the appropriate strength in wash buffer, added to the plates, and incubated for one hour at 37° C. Thereafter, dishes were washed three times with wash buffer. A conjugate Goat-anti-Mouse-Alexa448 (1:1.000) as second antibody, and a counter stain with Evans Blue (1:1.500) were added to the dishes in wash buffer and incubated for another hour at 37° C. The dishes were then washed three times with wash buffer. Finally, 44% glycerol in PBS was added to the dishes. Virus plaques were counted using a fluorescence microscope, and virus titers of the test samples were calculated in pfu/ml.

Results:

The results of the in-use stability test of the different alphaherpesviruses are presented in Table 5, as the titres in pfu/ml at the start of the test, and after 4 hours at room temperature. The column with the delta indicates the difference in titre between the two time points. The two panels of Table 5 allow the comparison of the results of the standard diluent, to those of the preferred invention diluent.

TABLE 5

Results of in-use stability testing of different alphaherpesviruses.

|  | Nobilis Diluent CA (10Log pfu/ml) | | | Invention diluent (10Log pfu/ml) | | |
|---|---|---|---|---|---|---|
| Test sample | T = 0 | T = 4 hr | Δ | T = 0 | T = 4 hr | Δ |
| Nobilis ® Rismavac | 6.0 | 5.8 | 0.2 | 6.0 | 5.8 | 0.2 |
| Innovax ® ILT | 6.9 | 6.5 | 0.4 | 6.8 | 6.4 | 0.4 |
| Innovax ® ND | 4.3 | 3.1 | 1.2 | 4.2 | 3.6 | 0.7 |
| Innovax ® ND-IBD | 7.1 | 6.7 | 0.4 | 7.0 | 6.7 | 0.3 |
| SB1 | 5.4 | 4.8 | 0.6 | 5.4 | 5.1 | 0.3 |
| FC126 | 6.8 | 6.2 | 0.6 | 6.7 | 6.4 | 0.4 |

As can be clearly observed, the loss of titre in the invention diluent was either the same or less compared to the standard diluent. This effect occurred for all the three virus types tested: HVT, MDV1 and MDV2. Loss of titre was in most cases no more than 0.410 Log pfu/ml, and usually less.

For one sample, Innovax ND, the loss in titre of 0.710 Log pfu/ml was quite large in the invention diluent, and exceeded the normal maximal loss of titre of 0.410 Log pfu/ml. However for this sample the loss in titre in the standard diluent was even much worse at 1.210 Log pfu/ml. As this was also the virus that needed the least dilution, this was probably not a good quality sample to begin with, and not representative of its kind, although it does show an impressive difference in stabilising capacity between the invention diluent and the standard diluent.

The invention claimed is:

1. A method for the in-use stabilization of cells infected with a cell-associated alphaherpesvirus, comprising admixing said infected cells with a protein-free diluent that comprises between 75 and 400 mM sugar and a phosphate buffer.

2. The method of claim 1, wherein the cell-associated alphaherpesvirus is of a genus selected from the group consisting of Mardivirus and Iltovirus.

3. The method of claim 1, wherein the cell-associated alphaherpesvirus is selected from the group consisting of Marek's disease virus and herpesvirus of turkeys.

4. The method of claim 1, wherein the cells are avian fibroblasts.

5. The method of claim 1, wherein the diluent has a pH in the range from about 7.0 to about 7.8.

6. The method of claim 1, wherein the sugar is sucrose.

7. The method for the in-use stabilization of cells infected with a cell-associated alphaherpesvirus of claim 1, wherein the protein-free diluent comprises between 100 and 300 mM sugar and a phosphate buffer.

8. A method for the in-use stabilization of cells infected with a cell-associated alphaherpesvirus, comprising admixing said infected cells with a protein free diluent that comprises a sugar and a phosphate buffer;

wherein the phosphate buffer has a pH in the range of about 7.0 to 7.5, and comprises about 1 to about 4 mM $KH_2PO_4$, and about 5 to about 9 mM $Na_2HPO_4$;

wherein the sugar is sucrose having a concentration of about 100 to 350 mM;

wherein the diluent further comprises about 50 to 250 mM sodium and about 0.01-0.02 mg/ml phenolsulfonphtalein; and wherein the cell-associated alphaherpesvirus is selected from the group consisting of Marek's disease virus and herpesvirus of turkeys.

9. The method of claim 8, wherein the cells are avian fibroblasts.

10. A vaccine against cell-associated alphaherpesvirus;

wherein the vaccine comprises cells infected with said alphaherpesvirus;

wherein the cells are suspended in a protein-free diluent that comprises between 75 and 400 mM sugar and a phosphate buffer.

11. The vaccine of claim 10, wherein the vaccine is for avians; and wherein the cell-associated alphaherpesvirus is selected from the group consisting of an Infectious Laryngotracheitis virus, a Marek's disease virus, and a herpesvirus of turkeys.

12. The vaccine of claim 10, wherein the cells are avian fibroblasts.

13. A method of preparing the vaccine of claim 10, comprising admixing cells infected with a cell-associated alphaherpesvirus and the protein-free diluent.

14. The method of claim 13, wherein the cells are avian fibroblasts.

15. The vaccine of claim 10, wherein the cells are suspended in a protein-free diluent that comprises between 100 and 300 mM sugar and a phosphate buffer.

* * * * *